United States Patent
Smith

(10) Patent No.: US 6,580,047 B1
(45) Date of Patent: Jun. 17, 2003

(54) APPARATUS FOR DESTROYING SYRINGE-TYPE NEEDLES BY ELECTRICAL CURRENT

(75) Inventor: Michael W. Smith, Roswell, GA (US)

(73) Assignee: Biomedical Disposal, Inc., Norcross, GA (US)

(*) Notice: Subject to any disclaimer, the term of this patent is extended or adjusted under 35 U.S.C. 154(b) by 0 days.

(21) Appl. No.: 09/442,332

(22) Filed: Nov. 17, 1999

Related U.S. Application Data

(60) Provisional application No. 60/108,767, filed on Nov. 17, 1998.

(51) Int. Cl.[7] ........................ B23K 11/22; A61G 12/00; A61L 11/00
(52) U.S. Cl. ........................................................ 219/68
(58) Field of Search ............................................ 219/68

(56) References Cited

U.S. PATENT DOCUMENTS

| | | | | |
|---|---|---|---|---|
| 5,138,124 A | | 8/1992 | Kirk et al. ................ | 219/68 |
| 5,468,928 A | * | 11/1995 | Yelvington ................ | 219/68 |
| 5,736,706 A | * | 4/1998 | Butler ....................... | 219/68 |
| 6,169,259 B1 | * | 1/2001 | Hall et al. .................. | 219/68 |
| 6,169,260 B1 | * | 1/2001 | Akutsu et al. ............. | 219/68 |
| 6,376,792 B1 | * | 4/2002 | Cebollero et al. ......... | 219/68 |

* cited by examiner

*Primary Examiner*—Geoffrey S. Evans
(74) *Attorney, Agent, or Firm*—Wayne J. Colton, Inc.

(57) ABSTRACT

The invention is directed to an apparatus for destroying metal needles having a shaft, hub, and a tip comprising first and second electrodes spaced in an overlapping relationship. The first electrode is generally disc shaped and the second electrode is generally cylindrically shaped. The apparatus also includes a power source connected across the first and second electrodes.

14 Claims, 5 Drawing Sheets

US 6,580,047 B1

APPARATUS FOR DESTROYING SYRINGE-TYPE NEEDLES BY ELECTRICAL CURRENT

Applicant claims the right to priority based on Provisional Patent Application No. 60/108,767 filed Nov. 17, 1998.

FIELD OF THE INVENTION

This invention relates generally to the field of sterilizing and destroying the hypodermic needle component of the syringe so as to render it safe for disposal. More particularly, this invention relates to a self-contained apparatus, having an improved electrode structure, which melts or vaporizes and sterilizes the hypodermic needle component of a syringe by passing electricity continuously along portions of the needle component until significantly all of the needle portion has been burned due to heat produced by the electrical resistance through the needle component.

BACKGROUND OF THE INVENTION

Current medical practice favors one-time use hypodermic needle syringes over reusable syringes. After a one-time use hypodermic needle syringe has been used, it must be disposed of properly. A used hypodermic needle syringe often poses a health hazard to any person coming into contact with a contaminated needle or syringe. The widespread exposure of contagious and fatal diseases multiplies this danger.

The most common method for disposing of used hypodermic needle syringes is a "sharps" container. A sharps container merely is a plastic container into which the used hypodermic needle syringes are placed. When the container is full, a cap is placed on the container and the container is disposed of. Typically, a service picks up the full sharps containers and disposes of the full containers either through incineration or in landfills. When destroyed in incinerators, the sharps container provides a sufficient method of disposal of the used hypodermic needle syringes. However, sharps containers suffer from several disadvantages. First, the used hypodermic needle syringes are not sterilized before being placed in the sharps container. This can lead to unintentional contact with a contaminated needle. Second, if the sharps containers are disposed of in a landfill, there always is the possibility that the sharps container can inadvertently open or be broken, thus exposing the contaminated needles.

In U.S. Pat. No. 4,628,269 to Ch'ing-Lung, a device is disclosed for severing a needle from its syringe. The Ch'ing-Lung device comprises a pair of spaced apart electrodes within a self-contained unit. The needle of the syringe is inserted into an opening in the unit until the base of the needle component is positioned between the two electrodes. When electricity is passed between the electrodes, the electricity causes the portion of the needle between the electrodes to melt, thus severing the needle from the syringe body. The needle portion falls into a collection means and can be disposed. The Ch'ing Lung device does not destroy the needle, but merely severs the needle from the syringe body. Therefore, the Ch'ing-Lung device does not eliminate the dangers of contamination from the end of the needle, nor the safety hazard obvious from having many loose needle heads in the unit.

A plastic syringe destruction device is disclosed in U.S. Pat. No. 4,860,958 to Yerman. The Yerman device employs a cylinder and piston compaction unit which uses heat to thermally smash complete plastic syringes, including the needle component, into a compacted mass. One or more plastic syringes are placed in the cylinder and the cylinder lid is closed. The syringes then are heated to temperatures between 100° C. and 200° C. to bring about melting of the syringes, as well as sterilization. The piston travels upwardly in the cylinder while the syringes are at a desired temperature, thus compacting the softened or molten plastic syringes into the compacted mass. The Yerman device suffers from several disadvantages, the most important of which is that the syringes are not raised to a temperature high enough to destroy the metal needle portion of the syringe. After the plastic syringes have been compacted into a mass, the metal needles typically protrude from the plastic mass, thus still posing a danger to the operator. Although the needles may have been sterilized, puncture wounds caused by the needles are neither desired nor healthy.

A hypodermic syringe needle destroying and sterilizing apparatus and method is disclosed in U.S. Pat. No. 4,877,934 to Spinello. The Spinello device is aimed specifically at destroying the metal needle portion of the hypodermic syringe by using electrical resistance heating between electrodes. The hypodermic needle is placed in a carrier which contacts the upper portion of the metal needle closest to the syringe barrel. The carrier then carries the syringe over an upwardly sloping second electrode. As the needle point contacts the second electrode, electricity passes from the second electrode through the metal needle into the first electrode, thus causing resistance heating of the metal needle. In theory, the electrical resistance heating melts and destroys the metal needle. However, in practice, the electrical resistance heating generally only softens the metal needle such that as the metal needle contacts the to upwardly sloping second electrode, the metal needle bends outward. Although the Spinello device may heat the metal needle to a temperature high enough to sterilize it, typically the metal needle remains and poses the same health and safety hazard any other sharp instrument has. Further, the Spinello device comprises many moving parts which have the potential of jamming and wearing.

U.S. Pat. No. 4,969,379 to Taylor et al. discloses a device that is essentially a syringe guillotine. The syringe is inserted into a receiving hole a certain distance, and a spring-biased piston is hand actuated forcing a cutting member down on the syringe. The process is repeated until the entire syringe has been cut into smaller portions, which portions fall to the bottom of the container. Obviously, the Taylor device suffers from the disadvantage that the syringe is not sterilized and the metal needle portion, although in smaller pieces, still presents a safety hazard. After the Taylor device is full of syringe portions, it must be disposed of in much, the same manner as the sharps containers.

An electrical syringe needle destroyer is disclosed in U.S. Pat. No. 5,336,862 to Yelvington, which has overcome some of the deficiencies of the above designs. This design operates by attempting to thoroughly burn and destroy significantly all of the needle portion of the syringe by continuously passing a sufficient amount of electricity through the needle, burning and destroying portions of the needle at a time. The destroying unit has two disc shaped electrodes. Presumably, any remaining needle portion, particularly the nub of the needle closest the syringe barrel, also has been heated, through electrical resistance heating, to a sufficient temperature for a sufficient period of time to sterilize any remaining needle portion. Unlike the prior art which acted upon only the base and tip of the needle, this design attempted to act only on a small portion of the needle at a time, eliminating the need for the high amperages and voltages required by the prior art, and eliminating the problem of needles breaking between the base and tip and needles welding themselves to the electrodes as frequently occurs in the prior art devices. However, due to the design of the disc shaped electrodes, making initial contact as well as maintaining constant contact with the two electrodes was difficult.

SUMMARY OF THE INVENTION

As embodied and broadly described herein, the invention is an apparatus for destroying metal needles having a shaft, hub, and a tip, comprising a first electrode and a second electrode, the first and second electrodes spaced apart in an overlapping relationship. The first electrode is generally disc shaped and the second electrode is generally cylindrically shaped. The apparatus further has a housing for the electrodes and for a power source, and having an orifice for receiving the needle, the first electrode overlapping the orifice.

The accompanying drawings, which are incorporated herein and constitute part of this specification, illustrate an embodiment of the invention, and, together with the description, serve to explain the principles of the invention.

BRIEF DESCRIPTION OF THE DRAWINGS

The accompanying drawings are included to provide a further understanding of the invention and are incorporated and constitute a part of this specification. The drawings illustrate an embodiment of the invention and together with the description serve to explain the principles of the invention in the drawings. In the drawings.

DESCRIPTION OF THE PREFERRED EMBODIMENT

Reference will now be made in detail to the present invention, an example of which is illustrated in the accompanying drawings.

Figure 1:
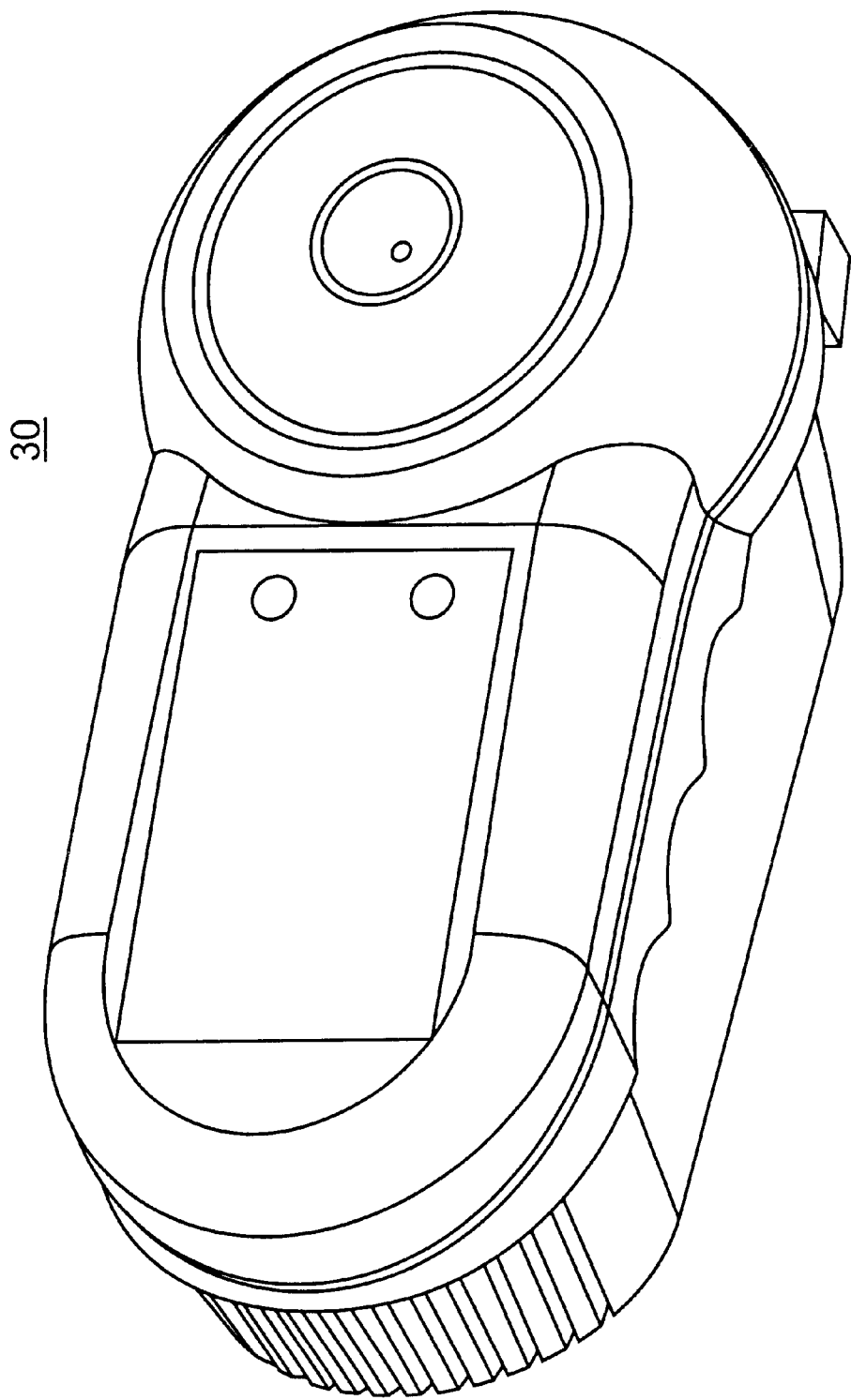
FIG. 1 is a perspective view of an embodiment of this invention.

The present invention, shown generally in FIG. 1, provides an apparatus which destroys significantly all of the metal needle portion of the hypodermic needle syringe.

Figure 2:
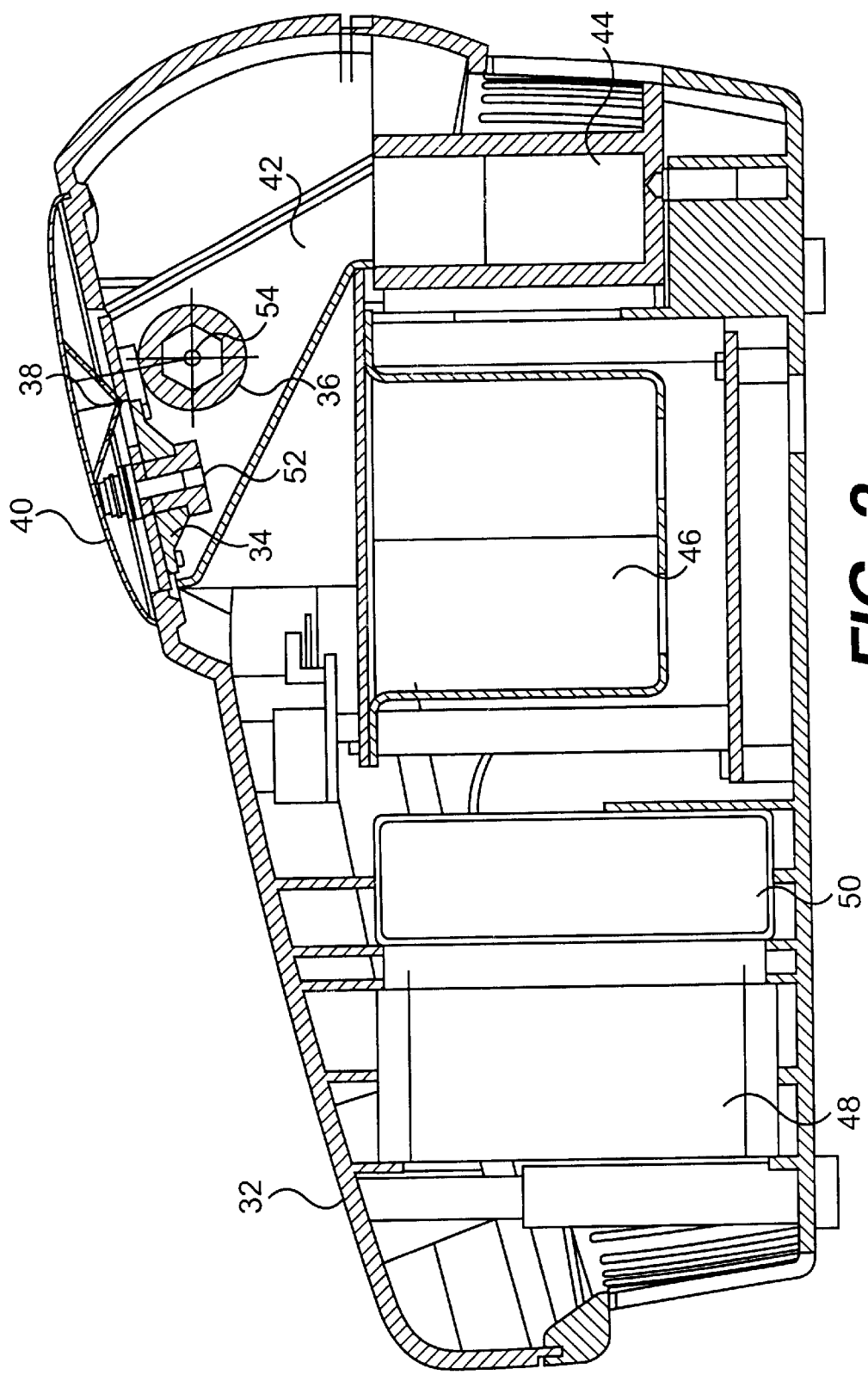
FIG. 2 is a cut-away side view of an embodiment of this invention.

In particular, as shown in FIG. 2, the needle destruction device 30 comprises a housing 32. The housing 32 contains a disc electrode 34, a roller electrode 36, and a needle orifice 38 for receiving a hypodermic needle for destruction. A dome 40 substantially covers the needle orifice 38 in the housing 32, thereby providing a passage in the housing for inserting a needle into the needle orifice. The housing 32 further contains an ash chute 42, a disposal drawer 44, a battery-powered electrode mechanical assembly 46, a filter 48, and a filter fan 50.

Figure 4:
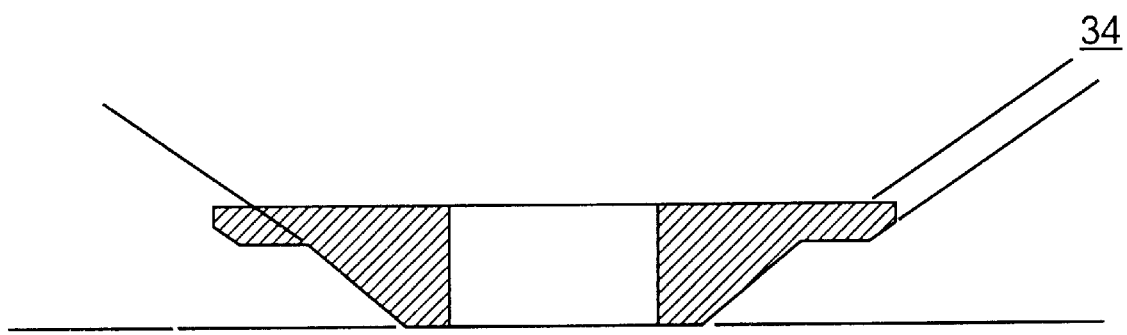
FIGS. 4 and 5 are detailed views of a disc electrode of the present invention.
Figure 5:
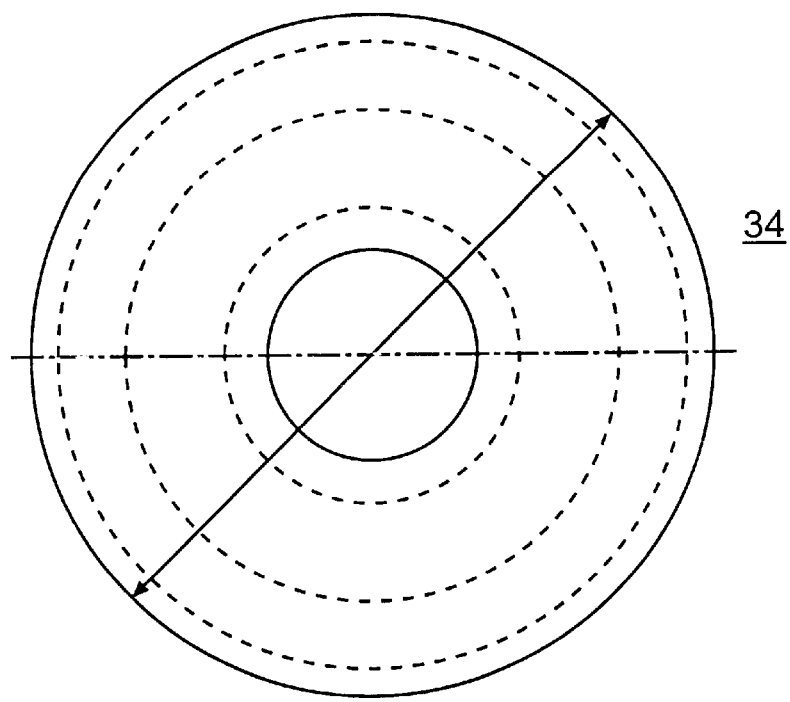
Figure 6:
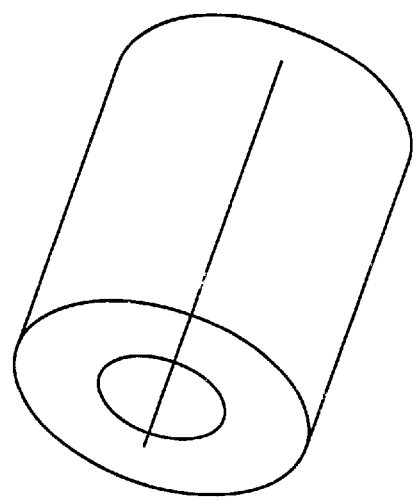
FIGS. 6 and 7 are detailed views of a roller electrode of the present invention.
Figure 7:
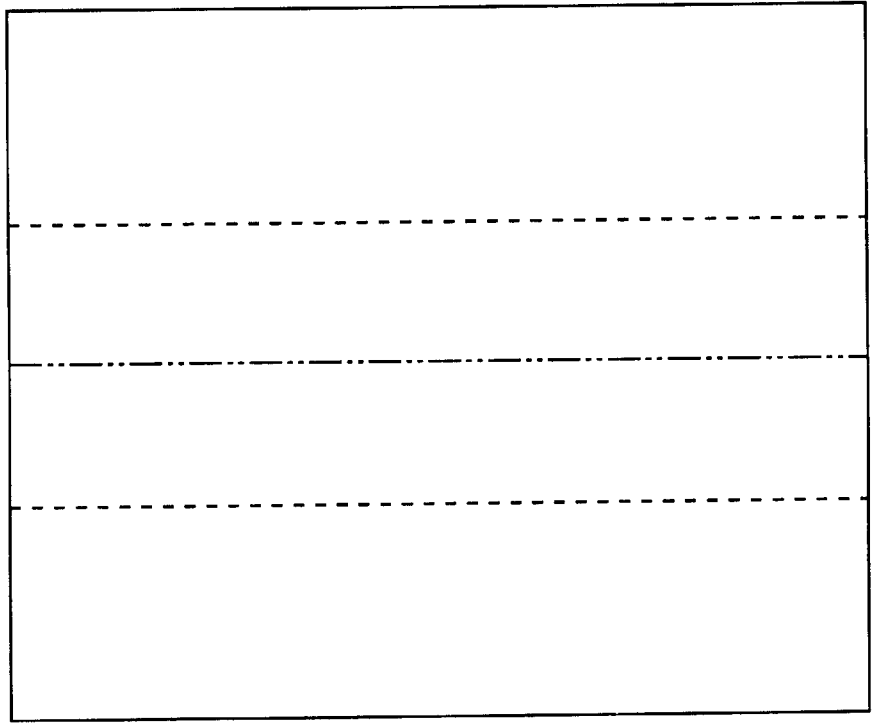

In particular, the disc electrode 34 of the present invention is positioned substantially adjacent to the needle orifice 38 located in the housing 32. The disc electrode 34 is rotationally journaled on a shaft 52. The shaft 52 is substantially perpendicular to the upper surface of the housing. The disc electrode 34, as shown in FIGS. 4 and 5, is generally disc-like in structure, having an upper surface, a circumferential surface, and a central, axial hole.

Figure 3:
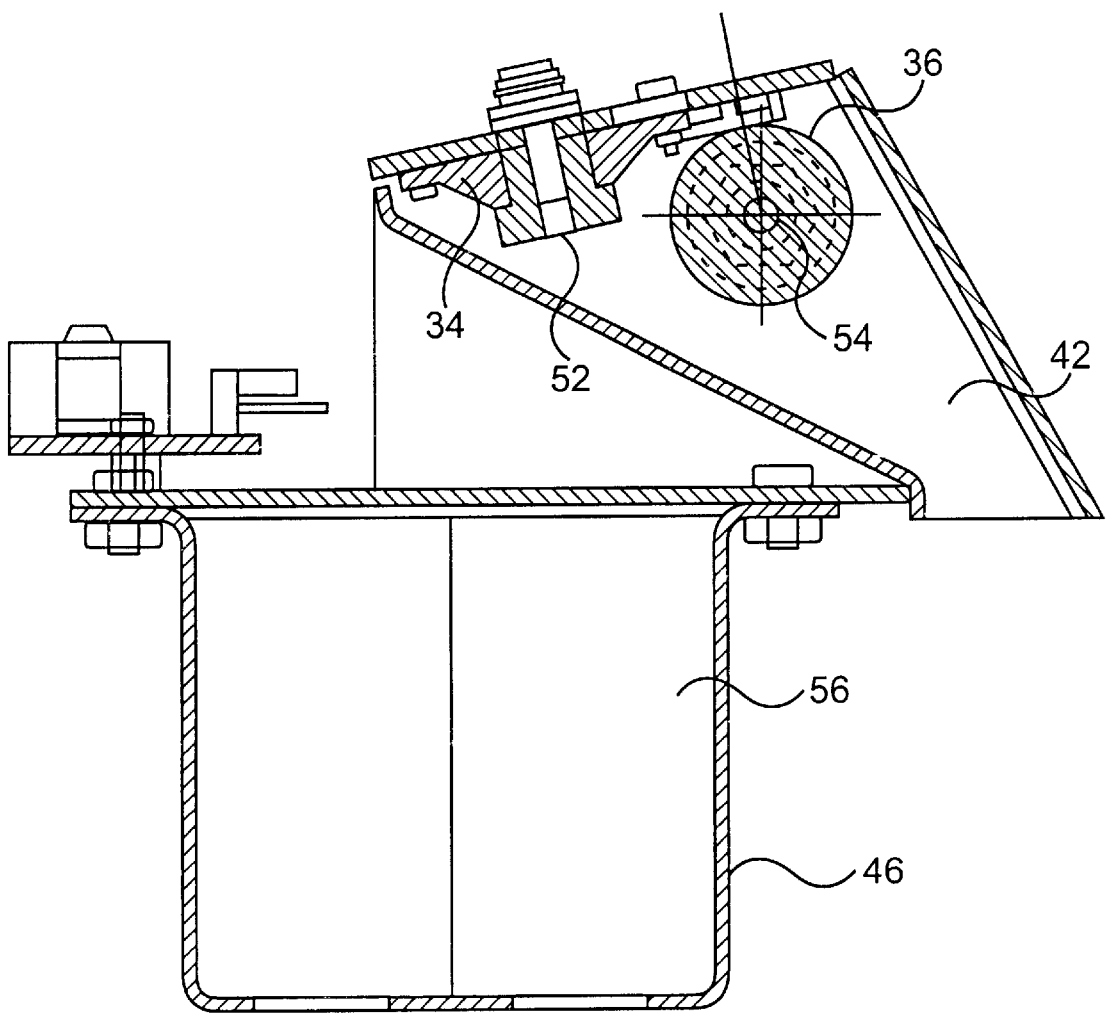
FIG. 3 is a detailed view of a feature in an embodiment of this invention.

In a preferred embodiment, the disc electrode has an outer diameter of between 0.850" and 1.150", and an overall height of between 0.150" and 0.200". It is further preferred that the lower portion of the disc electrode tapers inward towards the center. As shown in FIG. 3, the circumferential edge of the disc electrode overlaps the needle orifice 38, thereby allowing contact between the needle and the disc electrode as the needle is inserted through the needle orifice 38. It is preferred that this overlap be between 0.015" and 0.030".

The disc electrode 34 may be comprised of any suitable electrode material. In a preferred embodiment, the disc electrode is comprised of graphite. Those of ordinary skill in the art would know that material such as carbon, brass, tungsten, copper, beryllium copper, or titanium diboride, would also be sufficient.

In a preferred embodiment, the roller electrode has a diameter of approximately 0.500" to 0.750" and a length of approximately 0.500" to 1.000". In a more preferred embodiment the roller electrode 36 has an outer diameter of 0.625". The roller electrode 36 has a central, axial hole for accepting the shaft 54, wherein, in a preferred embodiment, the central, axial hole has a diameter of approximately 0.25". The roller electrode 36 is rotational and slidably mounted horizontally on a shaft 54. The roller electrode 36 may be comprised of any suitable electrode material. In a preferred embodiment the roller electrode 36 is fabricated of graphite. Those of ordinary skill in the art would understand that other material such as carbon, brass, tungsten, copper, beryllium copper, or titanium diboride, would also be sufficient.

The roller electrode is positioned in a substantially horizontal direction and is further positioned below the disc electrode 34. The disc electrode 34 overlaps the roller electrode 36. In a preferred embodiment, the disc electrode 34 overlaps the roller electrode 36 by between 0.100" and 0.250". It is preferred that the distance between the top surface of the disc electrode 34 and the center line of the roller electrode 36 be 0.3" to 0.5". In a more preferred embodiment, the distance from the top surface of the disc electrode to the center line of the roller electrode 36 is 0.400".

In a preferred embodiment, the roller electrode 36 is positioned relative to the disc electrode 34 such that approximately 0.100" to 0.250" of the needle is positioned between the disc electrode 34 and roller electrode 36 contact points. Those of ordinary skill in the art would understand that the length of the needle between the contact point varies with the needle gauge, whereby lower gauge larger diameter needles have a shorter length between the electrodes due to their larger needle diameter creating contact between the roller electrode 36 and disc electrode 34 closer to the needle orifice 38.

The disc electrode 34 and the roller electrode 36 are mounted to the electrode mechanical assembly 46 as shown in FIG. 2. Located underneath the disc electrode 34 and the roller electrode 36, and in the electrode mechanical assembly 46, is a battery. 56. The battery 56 can be any direct current electrical power source including, but not limited to, disposable batteries, rechargeable batteries, or an alternating current to direct current transformer. In a preferred embodiment a Ni-Cad battery pack is used that is capable of supplying 30–40 AMPS of current. Electrical current is produced by the battery 56 and is conducted through the hypodermic needle by contact with the disc electrode 34 and the roller electrode 36, wherein the disc electrode 34 is connected to the positive side of the battery pack 56, and the roller electrode 36 is connected to the negative side of the battery pack 56.

In operation, a used hypodermic needle is inserted into a needle orifice 38. The tip of the needle then makes contact with the roller electrode 36. The roller. electrode's 36 axis of rotation is offset from the needle orifice 38 such that the tip of the needle hits the roller electrode causing the roller to rotate downward along with the needle, thereby pushing the needle toward the disc electrode 34 and ensuring that the needle makes contact with both the disc electrode 34 and the roller electrode 36. simultaneously. As the needle comes into contact with the electrodes 34 and 36, direct current from the battery pack 56 flows through the needle resulting in a temperature increase generated from resistance heating.

The electrical current through the length of the needle between the electrodes 34 and 36 generates heat through resistive power dissipation, thereby raising the temperature of the needle to near its melting point. As the temperature increases, the metal begins to soften. As the needle is inserted into the needle orifice 38 for disposal, a downward force is applied with the following results: (1) heat sufficient to melt and/or vaporize some of the needle and organic material-inside the needle is generated; (2) as the needle material begins to soften, the pressure applied to the needle begins to flatten and collapse the portion of the needle in contact with the roller electrode 36; and (3) the needle is severed when the metal between the electrodes 34 and 36 softens and can no longer support its applied forces. As short portions of the needle are flattened and severed, the downward pressure causes the roller electrode 36 to continue to rotate. The roller electrode 36 rotation keeps the needle in contact with both electrodes 34 and 36 and also carries the severed molten portions of the needle to the ash chute 42. The needle debris then falls through the ash chute 42 and into the drawer 44. The needle is pushed down until the hub of the syringe makes contact with the dome 34. The needle hub is then removed from the unit and disposed of using appropriate disposal means. The needle debris resulting from the destruction process typically consists of ash and small fragments, approximately 0.050" in length. It is important to note that the current supply from the battery pack 58 must be sufficient to generate enough resistive heating in the length of needle between the electrodes to raise it close to its melting point, approximately 1371° C., in a relatively short period of time.

It is understood that the invention is not confined to the particular construction and arrangement of parts described herein but embraces such modified forms thereof as come within the scope of the following claims.

What is claimed is:

1. An apparatus for destroying a metal needle, said apparatus comprising:
    a disc-shaped electrode rotationally journaled on a first shaft and a roller-shaped electrode rotationally mounted on a second shaft, said disc-shaped electrode and said roller-shaped electrode being spaced apart in an overlapping relationship;
    a power source connected across said disc-shaped electrode and said roller-shaped electrode;
    a housing for said electrodes and said power source, said housing having an orifice for receiving the needle, said disc-shaped electrode overlapping said orifice; and
    wherein said second shaft is offset from said orifice such that insertion through said orifice of the needle results in rotation of said roller-shaped electrode.

2. The apparatus as recited in claim 1, wherein said second shaft is offset from said orifice such that insertion through said orifice of the needle results in rotation of said roller-shaped electrode.

3. The apparatus as recited in claim 1, wherein the rotation of said roller-shaped electrode resultant insertion of the needle pushes the needle toward said disc-shaped electrode.

4. An apparatus for destroying a metal needle, said apparatus comprising:
    a first electrode and a second electrode, said first and second electrodes being substantially enclosed within a housing having an orifice for receiving at least a portion of the needle;
    a power source connected across said first and second electrodes; and
    wherein:
        said first electrode is mounted within said housing adjacent to said orifice such that upon insertion through said orifice the needle may make contact with said first electrode; and
        said second electrode is rotationally mounted within said housing an axis of rotation, said axis of rotation being offset from said orifice such that insertion through said orifice of the needle results in rotation of said second electrode in a direction that pushes the needle toward said first electrode.

5. The apparatus as recited in claim 4, wherein said second electrode is roller-shaped.

6. The apparatus as recited in claim 4, wherein said second electrode is rotationally mounted about a shaft through said axis of rotation.

7. The apparatus as recited in claim 6, wherein said second electrode is roller-shaped.

8. The apparatus as recited in claim 4, wherein said first electrode rotationally mounted within said housing.

9. The apparatus as recited in claim 8, wherein said first electrode is journaled to said housing.

10. The apparatus as recited in claim 8, wherein said first electrode is rotationally mounted about a shaft, said shaft being dependently supported from said housing.

11. The apparatus as recited in claim 8, wherein said first electrode is disc-shaped.

12. The apparatus as recited in claim 11, wherein said first electrode is rotationally mounted about a shaft, said shaft being dependently supported from said housing.

13. The apparatus as recited in claim 8, wherein said first electrode overlaps said second electrode.

14. The apparatus as recited in claim 13, wherein:
    said second electrode is roller-shaped; and
    said first electrode overlaps said second electrode by approximately one third the radius of said second electrode.

* * * * *